US010548683B2

United States Patent
Chin et al.

(10) Patent No.: US 10,548,683 B2
(45) Date of Patent: Feb. 4, 2020

(54) SURGICAL PROCEDURE HANDHELD ELECTRONIC DISPLAY DEVICE AND METHOD OF USING SAME

(71) Applicant: KIC VENTURES, LLC, Malden, MA (US)

(72) Inventors: Kingsley Chin, Fort Lauderdale, FL (US); Aditya Humad, Cambridge, MA (US)

(73) Assignee: KIC VENTURES, LLC, Malden, MA (US)

( * ) Notice: Subject to any disclaimer, the term of this patent is extended or adjusted under 35 U.S.C. 154(b) by 293 days.

(21) Appl. No.: 15/438,336

(22) Filed: Feb. 21, 2017

(65) Prior Publication Data
US 2017/0239014 A1    Aug. 24, 2017

Related U.S. Application Data

(60) Provisional application No. 62/296,898, filed on Feb. 18, 2016.

(51) Int. Cl.
*A61B 90/00* (2016.01)
*G02B 27/01* (2006.01)
*A61B 90/20* (2016.01)

(52) U.S. Cl.
CPC .............. *A61B 90/37* (2016.02); *A61B 90/20* (2016.02); *G02B 27/0149* (2013.01); *G02B 2027/0159* (2013.01); *G02B 2027/0169* (2013.01)

(58) Field of Classification Search
CPC .... A61B 90/37; A61B 90/20; G02B 27/0149; G02B 2027/0169; G02B 2027/0159
See application file for complete search history.

(56) References Cited

U.S. PATENT DOCUMENTS

| 3,936,605 A | 2/1976 | Upton |
| 4,740,780 A | 4/1988 | Brown et al. |
| 5,013,135 A | 5/1991 | Yamamura |
| 5,214,413 A | 5/1993 | Okabayashi et al. |

(Continued)

FOREIGN PATENT DOCUMENTS

| CN | 202986989 | 6/2013 |
| DE | 102011120948 | 5/2013 |

(Continued)

OTHER PUBLICATIONS

Extended European Search Report dated Jan. 19, 2018 issued in corresponding European Application No. 14872906.4.

(Continued)

*Primary Examiner* — Nitin Patel
*Assistant Examiner* — Amy Onyekaba
(74) *Attorney, Agent, or Firm* — Onello & Mello LLP (57) ABSTRACT

In accordance with one aspect of the present disclosure, provided is a surgical heads-up display system comprising a heads-up display and an articulable arm coupled to the heads-up display. The heads-up display is configured to receive a portable electronic device and to redirect a display output of the portable electronic device. The articulable arm is configured to enable selective positioning and maintenance of the heads-up display in a selected position such that the display output of the portable electronic device is redirected in a chosen direction.

19 Claims, 8 Drawing Sheets

(56) References Cited

U.S. PATENT DOCUMENTS

| | | | |
|---|---|---|---|
| 5,325,975 A * | 7/1994 | Brown | A47B 87/0292 |
| | | | 211/189 |
| 5,394,203 A | 2/1995 | Murphy et al. | |
| 5,555,502 A | 9/1996 | Opel | |
| 5,677,701 A | 10/1997 | Okuyama et al. | |
| 5,878,395 A | 3/1999 | Bennett | |
| 5,905,477 A | 5/1999 | Kuwayama et al. | |
| 6,078,428 A | 6/2000 | Rambert et al. | |
| 6,209,767 B1 | 4/2001 | Liou | |
| 6,529,381 B1 | 3/2003 | Schoenfish | |
| 6,789,901 B1 | 9/2004 | Kormos | |
| 6,832,151 B2 | 12/2004 | Kumazaki et al. | |
| 7,111,996 B2 | 9/2006 | Seger et al. | |
| 7,126,583 B1 | 10/2006 | Breed | |
| 7,353,110 B2 | 4/2008 | Kim | |
| 7,565,180 B2 | 7/2009 | Tsai | |
| 7,623,294 B2 | 11/2009 | Harada et al. | |
| 7,734,414 B2 | 6/2010 | Gershony et al. | |
| 8,249,798 B2 | 8/2012 | Hawes et al. | |
| 8,301,108 B2 | 10/2012 | Naboulsi | |
| 8,503,762 B2 | 8/2013 | Ben Tzvi | |
| 8,698,858 B2 | 4/2014 | Kurozuka et al. | |
| 8,781,670 B2 | 7/2014 | Dolgov et al. | |
| 8,786,697 B2 | 7/2014 | Kawasaki | |
| 8,947,263 B2 | 2/2015 | Garay et al. | |
| 8,952,819 B2 | 2/2015 | Nemat-Nasser | |
| 9,205,816 B2 | 12/2015 | Kobana et al. | |
| 9,268,135 B2 | 2/2016 | Jan et al. | |
| 9,274,336 B2 | 3/2016 | Deubzer et al. | |
| 9,324,234 B2 | 4/2016 | Ricci et al. | |
| 9,395,544 B2 | 7/2016 | Luttmann et al. | |
| 9,596,096 B2 | 3/2017 | Taylor | |
| 9,884,591 B2 | 2/2018 | Hoek et al. | |
| 9,918,001 B2 | 3/2018 | Pisz | |
| 2002/0068605 A1 | 6/2002 | Stanley | |
| 2003/0043029 A1 | 3/2003 | Ichikawa et al. | |
| 2004/0160124 A1 | 8/2004 | Arai | |
| 2004/0164971 A1 | 8/2004 | Hayward et al. | |
| 2004/0204004 A1 | 10/2004 | Chen | |
| 2004/0209594 A1 | 10/2004 | Naboulsi | |
| 2006/0012884 A1 | 1/2006 | Snorteland | |
| 2006/0077497 A1 | 4/2006 | Harada et al. | |
| 2006/0261931 A1 | 11/2006 | Cheng | |
| 2007/0082713 A1 | 4/2007 | Tsai | |
| 2007/0217018 A1 | 9/2007 | Fredriksson | |
| 2007/0233376 A1 | 10/2007 | Gershony et al. | |
| 2008/0001727 A1 | 1/2008 | Ohsumi et al. | |
| 2009/0150061 A1 | 6/2009 | Chen et al. | |
| 2010/0268426 A1 | 10/2010 | Pathak et al. | |
| 2010/0320341 A1 | 12/2010 | Baumann et al. | |
| 2011/0001932 A1 | 1/2011 | Zuehlsdorff | |
| 2011/0093190 A1 | 4/2011 | Yoon | |
| 2012/0054401 A1 * | 3/2012 | Cheng | G06F 1/1632 |
| | | | 710/304 |
| 2012/0242724 A1 | 9/2012 | Kurozuka et al. | |
| 2013/0018549 A1 | 1/2013 | Kobana et al. | |
| 2013/0072787 A1 * | 3/2013 | Wallace | A61B 6/12 |
| | | | 600/424 |
| 2013/0108229 A1 | 5/2013 | Starner et al. | |
| 2013/0162515 A1 * | 6/2013 | Prociw | G06F 1/1616 |
| | | | 345/156 |
| 2013/0167159 A1 | 6/2013 | Ricci et al. | |
| 2014/0095294 A1 | 4/2014 | Vick et al. | |
| 2014/0121927 A1 | 5/2014 | Hanita | |
| 2014/0210625 A1 | 7/2014 | Nemat-Nasser | |
| 2014/0232564 A1 | 8/2014 | Garay et al. | |
| 2014/0267066 A1 | 9/2014 | Kolehmainen | |
| 2014/0313586 A1 | 10/2014 | Jan et al. | |
| 2014/0320973 A1 | 10/2014 | Deubzer et al. | |
| 2015/0054760 A1 * | 2/2015 | Amaru | G02B 27/0101 |
| | | | 345/173 |
| 2015/0062342 A1 | 3/2015 | Hoek et al. | |
| 2015/0260992 A1 | 9/2015 | Luttmann et al. | |
| 2015/0363348 A1 | 12/2015 | Deratany | |
| 2016/0057335 A1 | 2/2016 | Pisz | |
| 2016/0080163 A1 | 3/2016 | Taylor | |
| 2016/0086305 A1 | 3/2016 | Watanabe | |
| 2016/0341962 A1 | 11/2016 | Amaru et al. | |
| 2017/0174129 A1 | 6/2017 | Chin et al. | |
| 2017/0239014 A1 | 8/2017 | Chin et al. | |
| 2017/0305349 A1 | 10/2017 | Naboulsi | |
| 2017/0343805 A1 | 11/2017 | Amaru et al. | |
| 2018/0004473 A1 * | 1/2018 | Amaru | B60K 37/00 |

FOREIGN PATENT DOCUMENTS

| | | |
|---|---|---|
| FR | 2943431 | 9/2010 |
| KR | 20130036934 | 4/2013 |
| WO | 2015017693 | 2/2015 |
| WO | 2015095849 | 6/2015 |
| WO | 2015134840 | 9/2015 |
| WO | 2016123248 | 8/2016 |

OTHER PUBLICATIONS

International Search Report and Written Opinion dated Jun. 19, 2015 in corresponding PCT Application No. Application No. PCT/US2015/019113.
Colaner, Seth, "$99 SenseHUD Merely Beginning of SenseDriver's Push for Auto Display Platform Dominance". Dec. 31, 2014. Retrieved from the Internet: http://www.tomshardware.com/news/sensedriver-sensehud-99-copilot,28289.html.
EESR dated Mar. 6, 2017 issued in corresponding European Application No. 14831305.9.
ISRWO issued Apr. 7, 2015 in corresponding International Application No. PCT/US2014/71759.
Partial European Search Report dated Aug. 14, 2017 issued in corresponding European Application No. 14872906.4.
Search Report and Written Opinion dated Dec. 11, 2014 in related PCT application No. PCT/US2014/049225.
Cunningham, Wayne, "SenseHUD, the Smartphone-Powered Windshield Display". Jan. 6, 2015. Retrieved from the Internet: https://www.cnet.com/roadshow/auto/sensedriver-technologies-sensehud/preview/.
Eley, B. Magnetstick-Onperiscope Lense for Iphoneand Camera Phones Surfaces May 7, 2013, Retrieved from the internet : <URL: http://geardiary.com/2013/05/07/magnet-stick-on-periscope-lense-for-iphone-and-camera-phones-surfaces/>; paragraph 3; figure 2.
International Search Report dated Apr. 13, 2016 in related PCT Application No. PCT/US16/15187.
Kee, Edwin, "SenseHUD, Is the Ultimate Portable Head-Up Display". Jan. 7, 2015. Retrieved from the Internet: http://www.ubergizmo.com/2015/01/sensehud-is-the-ultimate-portable-head-up-display/.
Marks, Lester Victor, "SenseHUD Turns your Iphone into a portable heads-up display". Jan. 7, 2015. Retrieved from the Internet: http://appleinsider.com/articles/15/01/07/first-look-sensehud-turns-your-iphone-into-a-portable-heads.
Straub, S, "Gearing up to Battle Snow" 2, Heads up! Feb. 12, 2014. Retrieved from the Internet: <URL: https://seancrosspoints.wordpress.com/2014/02/12/GEARING-UP-TO-BATTLE-SNOW-2-HEADS-UP/>; paragraph 7.
European Office Action dated Feb. 22, 2018 issued in corresponding European Application No. 14831305.9.
Chinese Office Action dated May 8, 2018 issued in corresponding Chinese Application No. 201480054192.2, with English language summary.

* cited by examiner

SURGICAL PROCEDURE HANDHELD ELECTRONIC DISPLAY DEVICE AND METHOD OF USING SAME

CROSS-REFERENCE TO RELATED APPLICATIONS

This application claims the benefit, under 35 U.S.C § 119(e), to U.S. Provisional Patent Application No. 62/296,898, entitled SURGICAL PROCEDURE HANDHELD ELECTRONIC DISPLAY DEVICE AND METHOD OF USING SAME, filed on Feb. 18, 2016, in the United States Patent and Trademark Office, the disclosure of which is incorporated herein in its entirety by reference.

FIELD OF INTEREST

The present inventive concepts relate to the field of medical equipment, and more particularly to the field of equipment useful to a surgeon in various medical procedure.

BACKGROUND

In the field of surgery, various types of electro-mechanical apparatuses can be useful for assisting a surgeon in performing complex procedures. In some case, a surgical area can be relatively small and a surgeon's view or perspective of such an area can be somewhat physically limited. It would be further useful to provide an apparatus that can provide information capture, storage, and sharing in such a surgical setting.

SUMMARY

In accordance with aspects of the inventive concept, provided is a surgical heads-up display system comprising a heads-up display (HUD) that includes a dock configured to receive and maintain a smartphone and/or tablet in substantially horizontal position that leaves a camera and a display of the smartphone unobstructed, the HUD further including a display medium configured to selectively redirect a display output of the smartphone. The system also includes an articulable arm having at least one articulable joint, and having a first end configured to couple to the heads-up display and a second end mount to configured to couple to a treatment surface, including an operating table, wherein the articulable arm is configured to enable positioning and maintenance of the heads-up display in a selected position relative to the treatment surface.

In some embodiments, the articulable arm includes a first end removably coupled to the heads-up display.

In some embodiments, the articulable arm second end mount is configured to rest upon a surface.

In some embodiments, the articulable arm second end mount is configured to couple to a surface, structure, or apparatus.

In some embodiments, the second end mount includes a table mount, bed mount, cart mount, or wall mount.

In some embodiments, the second end mount includes a clamp.

In some embodiments, the system further comprises an articulable joint coupling the second end mount with the articulable arm.

In some embodiments, the articulable arm includes two or more arm segments connected by one or more articulable joint.

In some embodiments, the articulable arm includes three or more arm segments connected by two or more articulable joints.

In some embodiments, the articulable arm second end includes a post arm segment.

In some embodiments, the post arm segment is a substantially vertical post.

In some embodiments, the post arm segment is a height-adjustable post.

In some embodiments, the height-adjustable post is a telescoping post.

In some embodiments, the post arm segment is not rotatable with respect to the second end mount.

In some embodiments, the post arm segment is rotatable with respect to the mount.

In some embodiments, the articulable joint or joints can enable up to a 360 degree rotation.

In some embodiments, the at least one articulable joint enables two or more degrees of freedom.

In some embodiments, the display medium is configured for orientation at an angle of between about 0 and about 60 degrees or less with respect to the display frame or the display of the portable electronic device disposed in the heads-up display.

In some embodiments, the system includes a surgical heads-up display computer program product ("HUD application") configured for storage on and execution by the smartphone and/or tablet to a least partially control function of the camera and/or the display of the smartphone and/or tablet.

In some embodiments, the HUD application enables, in response to a voice control command, one or more of: received text messages to be read out loud; phone calls to be placed, conducted, and/or answered; voice to text messages to be generated and sent to contacts; a light of the portable electronic device to be selectively turned on/off; pictures to be taken with a camera of the portable electronic device; video to be recorded with a camera of the portable electronic device, and/or a camera of the portable electronic device to zoom in/out.

In accordance with aspects of the inventive concept, provide is a system, apparatus, and method that are useful for providing a surgeon and/or surgical staff with the ability to view, record, and share surgical information. Image and video capture as well as magnification can be provided.

Such an apparatus can include a display and camera and can be physically manipulatable, so that a user can orient and reorient the camera and the display as needed. The apparatus can be networkable, so that surgical information, e.g., video and images, can be captured, stored, and shared. This capability can also be configured to enable the surgeon and/or surgical staff to receive or otherwise display useful information, such as via one or more of text, images, videos, and/or audio. Such information could include instructions or other content useful for performing certain procedures or treating the patient.

In this regard, the apparatus can be configured to aid a surgeon, or other surgical staff, in performing complex medical procedures. Such aid may come in the form of providing a different viewing angle and/or magnification of the surgical area. If such device has image capture and/or image recording capability, it can be further useful for various purposes, historical recording, training, or post-op analysis. And if such an apparatus can communicate such videos, images, or other information over a computer network, it may be further useful.

In accordance with one aspect of the inventive concept, provided is a surgical heads-up display system, comprising a portable electronic device dock in combination with a projection medium and an articulable arm configured to enable a user to position the dock in a selected position relative to a treatment zone. When in the selected position, the dock and projection medium cooperate to project or reflect images and or video of the treatment zone taken by at least one camera of a docked electronic device and output by a display of the docked electronic device.

In some embodiments, the portable electronic device can be a cellular telephone, electronic tablet, or camera with display.

In some embodiments, the dock comprises a compartment configured to receive the portable electronic device without obstructing the display or the at least one camera of the electronic device.

In some embodiments, the compartment includes: a frame having left and right channels configured to receive top and bottom portions of the electronic device; a display window defined within the frame that provides unobstructed transmission of the display of the docked electronic device; and a camera window defined within the frame that provides unobstructed access to the treatment zone by the at least one camera of the docked electronic device.

In some embodiments, the dock includes: at least one audio-transmissive-speaker conduit configured to receive audio from a speaker of the docked electronic device; and at least one audio-transmissive-microphone conduit configured to channel external audio to a microphone of the docked electronic device.

In some embodiments, the projection medium is oriented with respect to the display of the docked electronic device at an angle of about 45 degrees in a use position.

In some embodiments, a projection angle of the projection medium is about 90 degrees with respect a transmission path from the display window and/or display of the docked electronic device.

In some embodiments, the projection medium is coupled to the dock.

In some embodiments, the projection medium is coupled to the dock via at least one hinge.

In some embodiments, the at least one hinge enables the projection medium to be oriented with respect to the display window and/or the display of the docked electronic device at an angle of in a range of about 0 to 90 degrees.

In some embodiments, the hinge is configured with one or more stop positions, wherein each stop position defines a preset angle of rotation of the projection medium with respect to the display window and/or the display of the docked electronic device.

In some embodiments, one stop position is at about 45 degrees with respect to the display window and/or the display of the docked electronic device.

In some embodiments, one stop position is at about 0 degrees with respect to the display window, which is a closed position that protects the projection medium.

In some embodiments, the dock and projection medium are arranged to project or reflect images and/or video to a user that are received from a horizontal capture position of the camera of the docked electronic device.

In some embodiments, the projection medium is oriented to project or reflect the images and/or video in a direction that is parallel to the horizontal orientation of the docked electronic device.

In some embodiments, the articulate arm is configured to maintain the dock above a patient in the treatment zone so that the camera of the docked electronic device is oriented above the patient while the projection medium is arranged to project images from the display of the docked electronic device in a substantially horizontal direction for viewing by a user.

In some embodiments, the articulate arm is a mechanical arm, an electro-mechanical arm, or a robotic arm, in either case having a plurality of degrees of freedom.

In some embodiments, the articulate arm has a first end coupled to the dock and a second end including a connector configured to couple to a surface or object.

In some embodiments, the connector is a vice clamp, a suction cup, a scissor clamp, or a nut and bolt.

In some embodiments, the projection medium includes one or more of a beam splitter, combiner glass, active mirror, passive mirror, semi-transparent mirror, an electrically switchable trans-reflective mirror, and/or remote display system.

In some embodiments, the projection medium is powered by a battery of the dock, the docked electronic device, or a dedicated battery.

In some embodiments, the content includes a 2D and/or 3D representation of a living patient or portion thereof.

In some embodiments, the content includes a 2D and/or 3D representation of a cadaver, a simulated patient, and/or a patient model, or portion of either of the foregoing.

In some embodiments, the content includes a computer generated 2D and/or 3D representation of an actual or simulated patient, or a portion of either of the foregoing.

In some embodiments, the user is a surgeon or other medical professional performing a medical procedure on a patient in the treatment zone.

In some embodiments, the user is a surgeon or other medical professional teaching a medical procedure on a real or simulated patient in the treatment zone.

In some embodiments, the user is a surgeon or other medical professional practicing a medical procedure on a simulated patient in the treatment zone.

In some embodiments, the content includes medical diagnostic and/or treatment information, including real-time and/or pre-existing images and/or video of a patient in the treatment zone.

In some embodiments, the content includes medical diagnostic and/or treatment information comprising pre-existing images and/or video.

In some embodiments, the content includes treatment information comprising educational images and/or video of a medical or surgical procedure relevant to the treatment information.

In some embodiments, the system further comprises a computer program product executable by at least one processor of the docked electronic device, the dock, or both, the executed computer program product configured to operatively control at least one of the display and the at least one camera of the docked electronic device.

In some embodiments, the computer program product includes a voice control module configured to control operations of the docked electronic device in response to a voice command.

In some embodiments, the voice control module is configured to control features of the display and/or camera of the docked electronic device.

In some embodiments, the voice control module is configured to control camera functions of the docked electronic device, including one or more of zoom in and out, resolution adjustment, flash on/off, image capture, and/or video capture.

In some embodiments, the voice control module is configured to control display functions of the docked electronic device, including one or more of zoom in and out, image select, image display, image save, image delete, image transmit, image print, color adjust, brightness adjust, image enhancement, and/or image orientation adjust, such as rotate, portrait, landscape.

In some embodiments, the voice control module is configured to control display functions of the docked electronic device, including one or more of video select, video play, video stop/pause, video save, video fast forward, video rewind, video delete, video transmit, video print, color adjust, brightness adjust, video enhancement, and/or video orientation adjust, such as rotate, portrait, landscape.

In some embodiments, the voice control module is configured to initiate and/or answer a phone call on the docked electronic device in response to a voice command.

In some embodiments, the voice control module is configured to cause the docked electronic device to search one or more database, library, or system for medical diagnostic or treatment information in response to a voice command and to present such medical diagnostic or treatment information via the projection medium.

In some embodiments, the search includes a search of one or more of an intranet, the Internet, or a virtual private network.

In some embodiments, the computer program product further comprises a text-to-speech module configured to read text from the docked electronic device.

In some embodiments, the computer program product further comprises a speech-to-text module configured to generate text from speech received by the docked electronic device.

In some embodiments, the projection medium includes multiple outputs rendering all or a portion of the display of the docked electronic device.

In some embodiments, the computer program product further comprises a display transmission module, configured to output all or a portion of the display of the docked electronic device to one or more remote displays and/or display systems.

In some embodiments, the one or more remote displays and/or display systems includes a surgical microscope to add more magnification or transfer images to the microscope processing system.

In some embodiments, the display transmission module enables the user to use the microscope for viewing and/or capturing images and/or video of the electronic device.

In accordance with one aspect of the present disclosure, provided is a surgical heads-up display system comprising a heads-up display and an articulable arm coupled to the heads-up display. The heads-up display is configured to receive a portable electronic device and to redirect a display output of the portable electronic device. The articulable arm is configured to enable selective positioning and maintenance of the heads-up display in a selected position such that the display output of the portable electronic device is redirected in a chosen direction.

In some embodiments, the portable electronic device is as a smartphone, tablet, phablet, or similar device, as examples.

In some embodiments, the articulable arm includes a first end removably coupled to the heads-up display.

In some embodiments, the articulable arm includes a second end distal from the first end, the second end having a mount configured to rest upon a surface.

In some embodiments, the articulable arm includes a second end distal from the first end, the second end having a mount configured to couple to a surface, structure, or apparatus.

In some embodiments, the articulable arm second end mount is configured to removably attach to a patient support apparatus, such as a bed, chair, or table.

In some embodiments, the articulable arm second end mount is a table mount, bed mount, cart mount, or wall mount.

In some embodiments, the articulable arm second end mount can include or take the form of a clamp, such as a spring clamp, for example.

In some embodiments, an articulable joint couples the second end mount with the articulable arm.

In some embodiments, the articulable arm can include two or more arm segments connected by one or more articulable joints.

In some embodiments, the articulable arm can include three or more arm segments connected by two or more articulable joints.

In some embodiments, the articulable arm can include a post arm segment coupled to the mount.

In some embodiments, the post arm segment can be a substantially vertical post.

In some embodiments, the post arm segment can be a height-adjustable post.

In some embodiments, the height-adjustable post can be a telescoping post.

In some embodiments, the post arm segment is not rotatable with respect to the mount, while in other embodiments, the post arm segment can be rotatable with respect to the mount.

In some embodiments, the articulable joint or joints can enable up to a 360 degree rotation.

In some embodiments, the articulable joint or joints can enable up to a 180 degree rotation.

In some embodiments, the articulable joint or joints can enable two or more degrees of freedom.

In some embodiments, the articulable joint or joints can include one or more hinge (e.g., a pin hinge) and/or one or more ball joint.

In some embodiments, the heads-up display includes a dock configured to maintain the portable electronic device within the heads-up display.

In some embodiments, the dock includes a support platform configured to support to the portable electronic device.

In some embodiments, the dock and/or the support platform includes a camera opening configured to reveal a camera of the portable electronic device when disposed and/or maintained in the dock.

In some embodiments, the dock can include a display frame configured to form a display opening revealing a display screen of the portable electronic device when disposed and/or maintained in the dock.

In some embodiments, the dock and/or the display frame can include one or more audio transmission paths or openings configured to receive audio output from the portable electronic device in the dock and to transmit the audio output external to the dock.

In some embodiments, the heads-up display includes a display medium configured to received and redirect the display output from the portable electronic device disposed or maintained in the heads-up display.

In some embodiments, the display medium can be configured to project the display output of the portable electronic device.

In some embodiments, the display medium can be configured to reflect the display output of the portable electronic device.

In some embodiments, the display medium can be configured for orientation at an angle of between about 0 and less than 90 degrees with respect to the display frame or the display of the portable electronic device disposed in the heads-up display.

In some embodiments, the display medium can be configured for orientation at an angle of between about 0 and about 60 degrees or less with respect to the display frame or the display of the portable electronic device disposed in the heads-up display.

In some embodiments, the display medium can be configured for orientation at an angle of between about 0 and about 45 degrees or less with respect to the display frame or the display of the portable electronic device disposed in the heads-up display.

In some embodiments, the display medium can be configured for orientation at an angle of between about 30 and about 60 degrees or less with respect to the display frame or the display of the portable electronic device disposed in the heads-up display.

In some embodiments, the display medium can be configured for orientation at an angle of 45 degrees or about 45 degrees with respect to the display frame or the display of the portable electronic device disposed in the heads-up display.

In some embodiments, the display medium is connected to the dock and/or display frame by at least one hinge.

In some embodiments, the hinge includes one or more preset stop positions for orienting the reflective medium at one or more predetermined angles.

In some embodiments, the hinge includes a 0 degree or closed stop position.

In some embodiments, the hinge includes a 45 degree stop position.

In some embodiments, the display medium is configured to close the display opening.

In some embodiments, the angle of the display medium with respect to the display frame is user adjustable.

In some embodiments, the display medium is or includes at least one of an active or a passive mirror.

In some embodiments, the display medium is or includes a beam splitter.

In some embodiments, the dock includes a dock opening configured to slidably receive the portable electronic device.

In some embodiments, the dock opening can be a side opening configured to laterally receive the portable electronic device.

In some embodiments, the dock opening can be a top or bottom opening configured to longitudinally receive the portable electronic device.

In some embodiments, the system includes a surgical heads-up display computer program product and/or computer application (collectively, "heads-up display application" or "HUD application") configured for storage on and execution by the portable electronic device.

In some embodiments, the HUD application enables voice command control of the portable electronic device.

In some embodiments, the HUD application enables voice command control of the camera, display, applications, and/or communications of the portable electronic device.

In some embodiments, the HUD application enables received text messages to be read out loud.

In some embodiments, the HUD application enables phone calls to be made, conducted, and/or answered.

In some embodiments, the HUD application enables voice to text messages to be generated and sent to contacts.

In some embodiments, the HUD application enables a light of the portable electronic device to be selectively turned on/off.

In some embodiments, the HUD application enables pictures to be taken with a camera of the portable electronic device.

In some embodiments, the HUD application enables video to be recorded with a camera of the portable electronic device.

In some embodiments, the HUD application enables a camera of the portable electronic device to zoom in/out.

In accordance with aspects of the inventive concepts, provided is a surgical heads-up display system as shown and described.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings.

DETAILED DESCRIPTION OF PREFERRED EMBODIMENTS

Various aspects of the inventive concepts will be described more fully hereinafter with reference to the accompanying drawings, in which some exemplary embodiments are shown. The present inventive concept may, however, be embodied in many different forms and should not be construed as limited to the exemplary embodiments set forth herein.

It will be understood that, although the terms first, second, etc. are be used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device may be otherwise oriented (e.g., rotated 90 degrees or at other orientations) and the spatially relative descriptors used herein interpreted accordingly.

Exemplary embodiments are described herein with reference to cross-sectional illustrations that are schematic illustrations of idealized exemplary embodiments (and intermediate structures). As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

To the extent that functional features, operations, and/or steps are described herein, or otherwise understood to be included within various embodiments of the inventive concept, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

Figure 1:
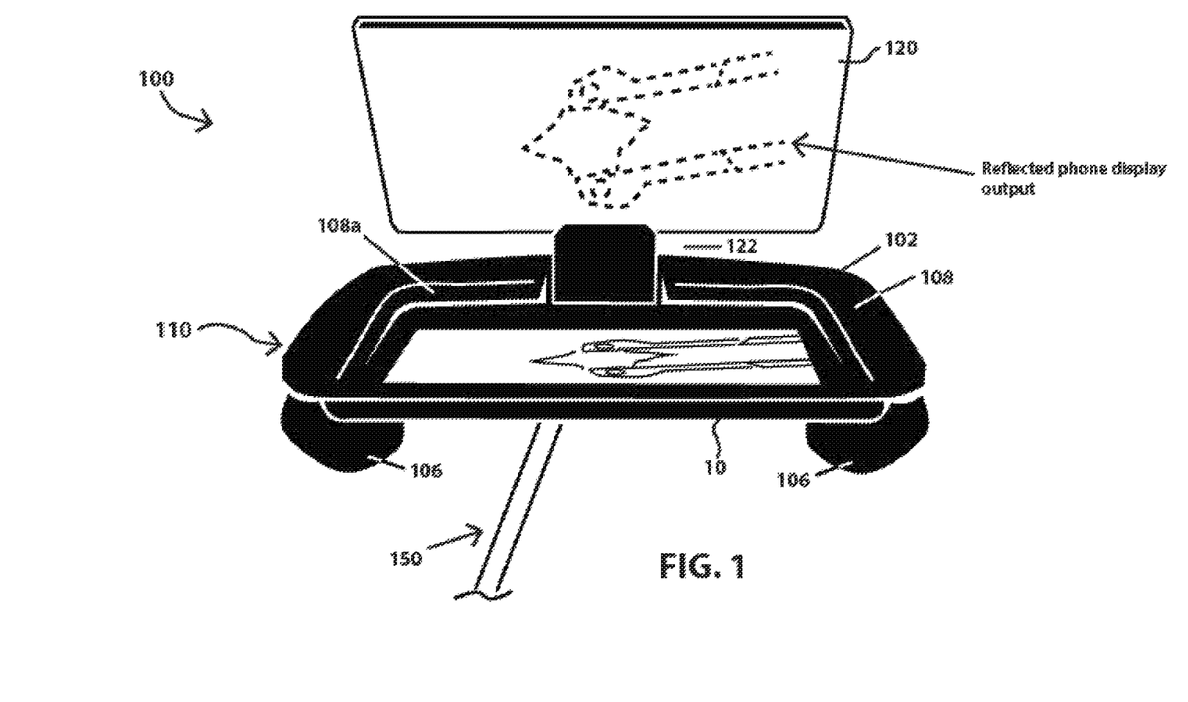
FIG. 1 is a front view of an embodiment of a surgical heads-up display apparatus in combination with a portable electronic device, in accordance with aspects of the inventive concept.
Figure 1A:
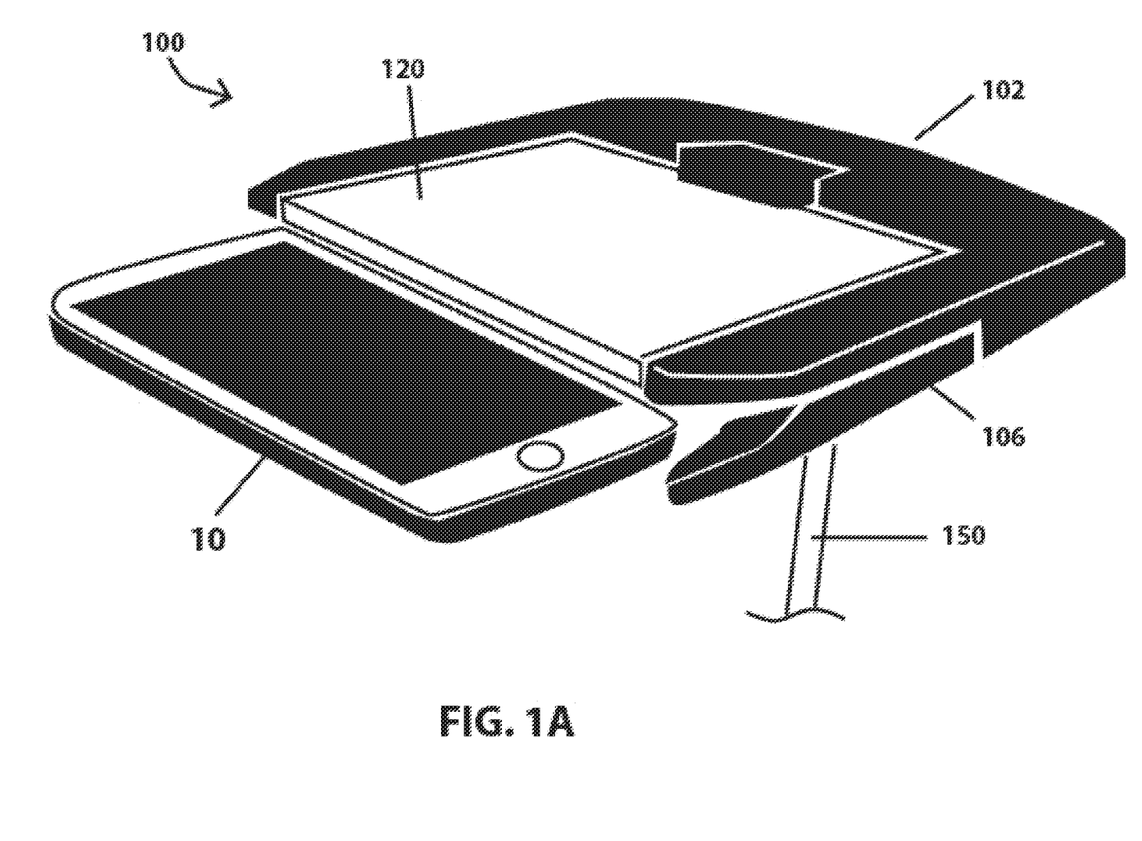
FIGS. 1A through 1D are different views of a heads-up display.
Figure 1B:
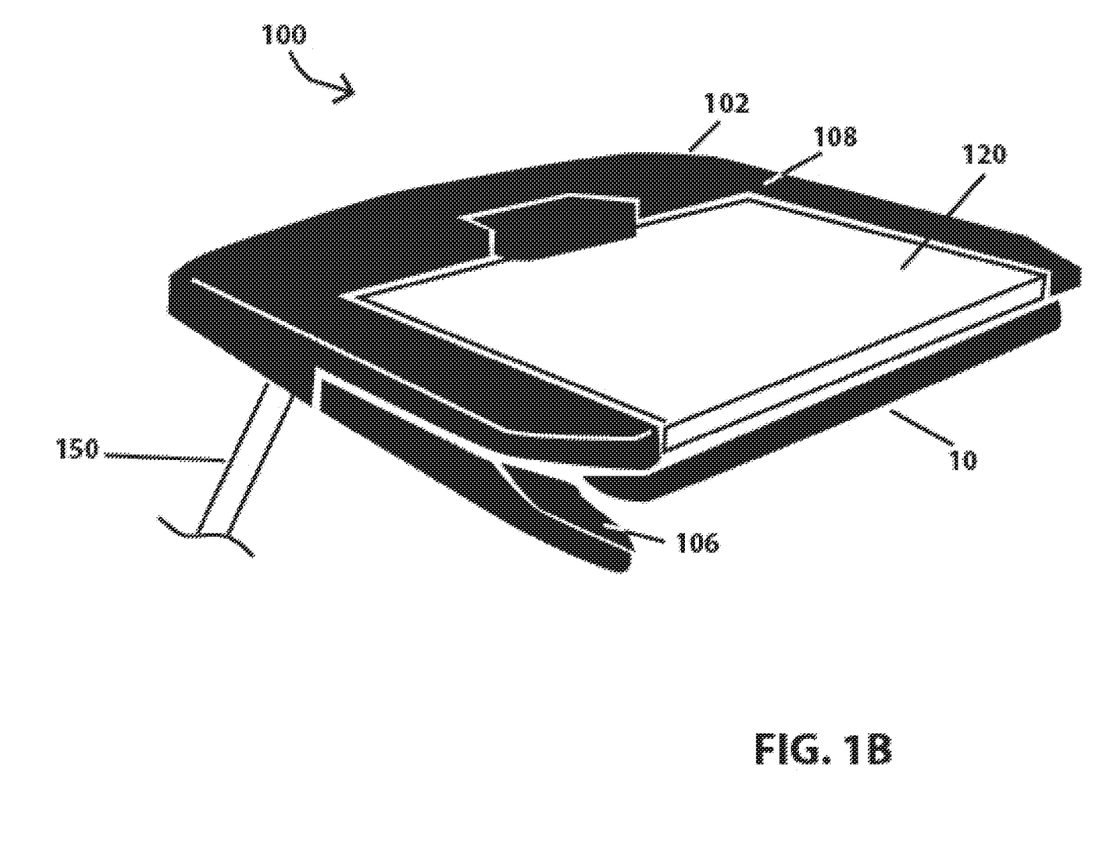
Figure 1C:
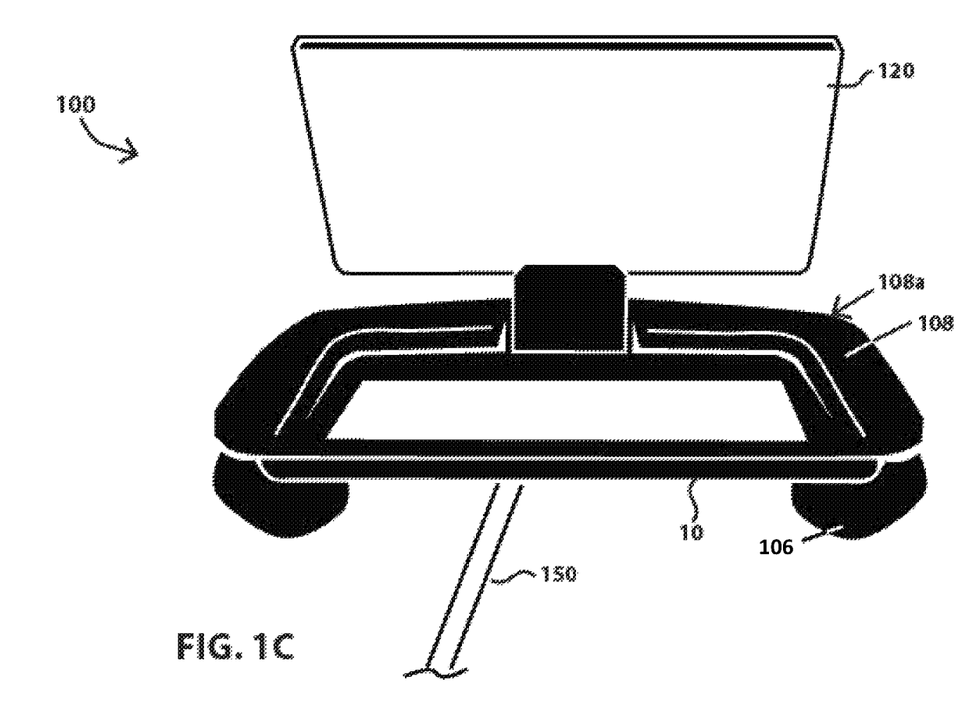
Figure 1D:
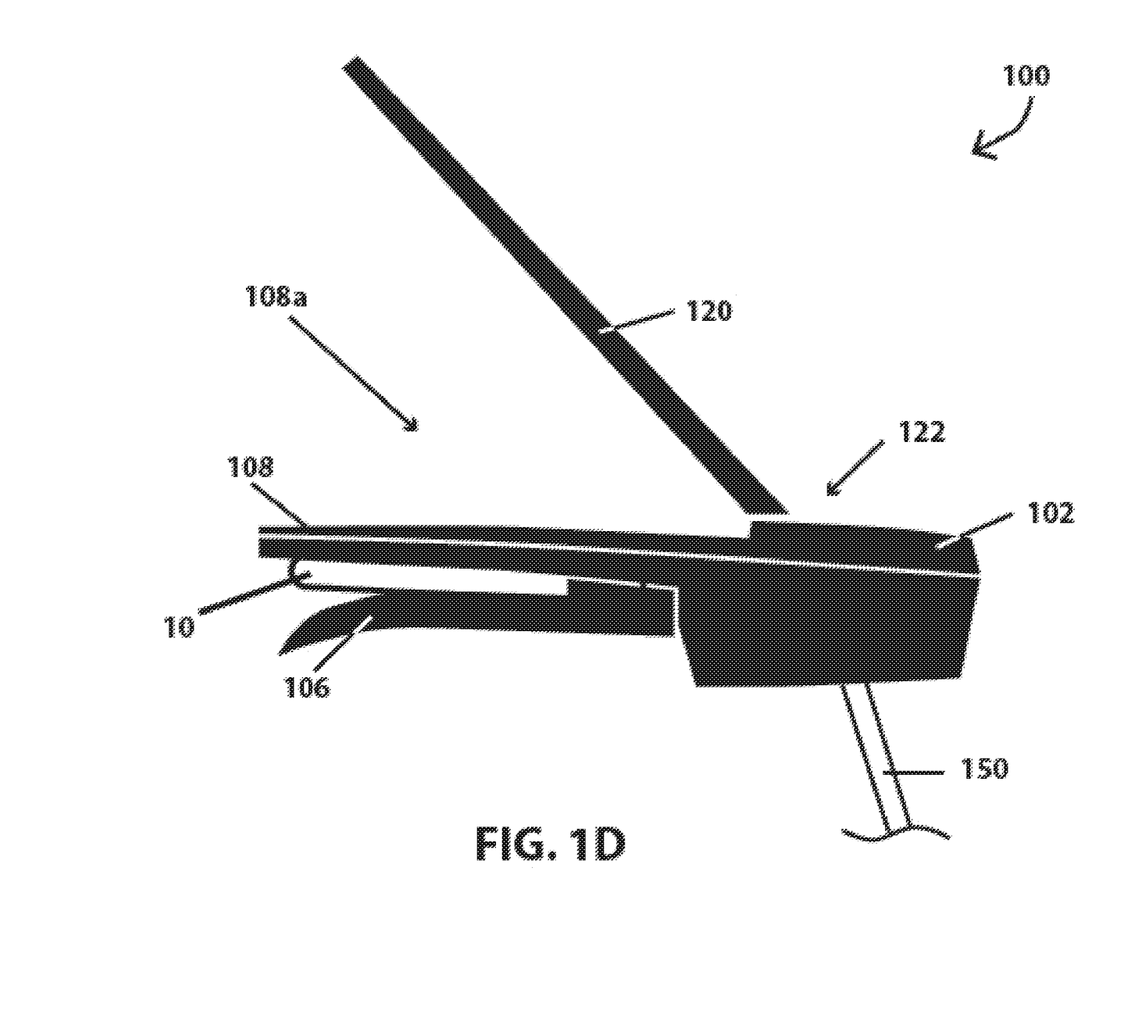
Figure 2:
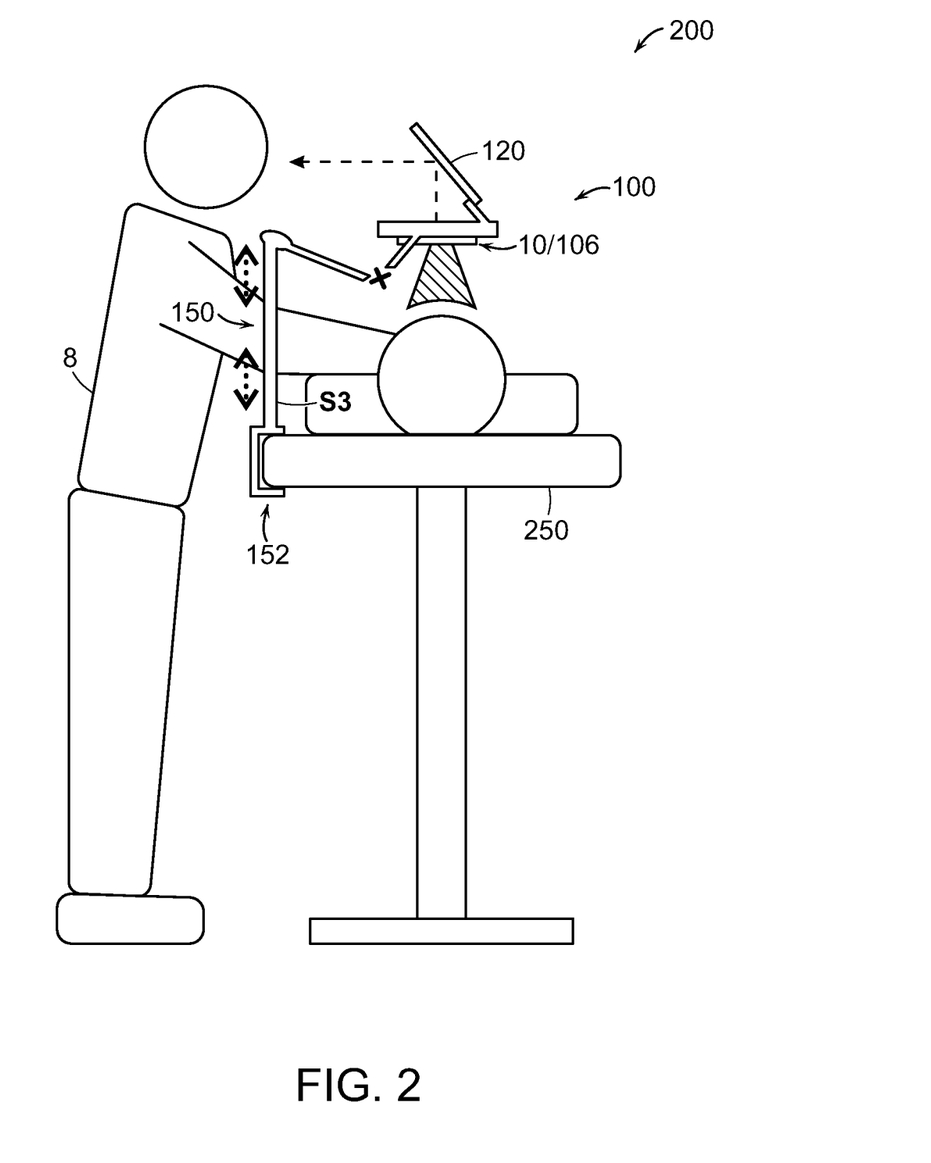
FIG. 2 is a side view of an embodiment of a surgical heads-up display system, in accordance with aspects of the inventive concept.
Figure 3:
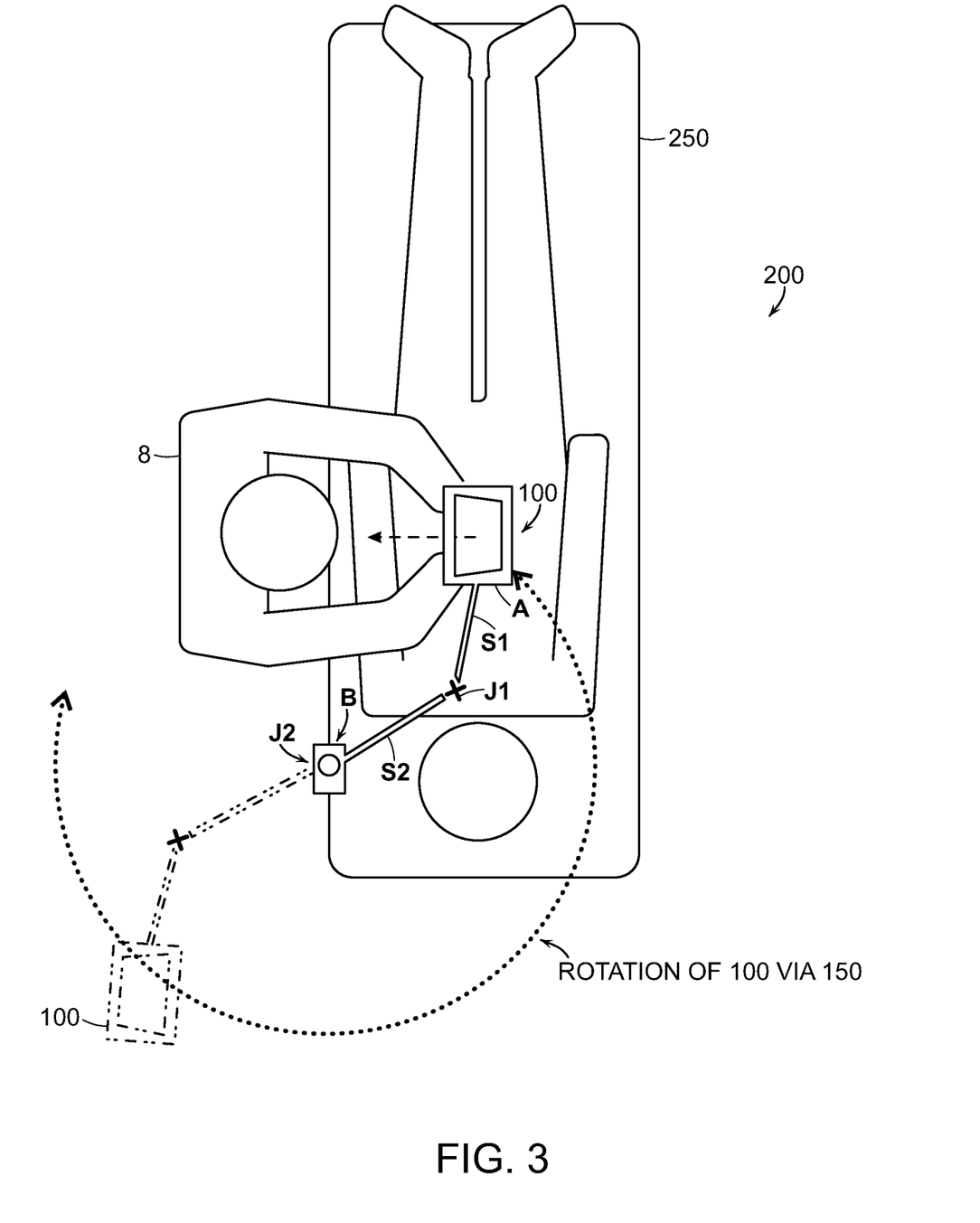
FIG. 3 is a top view of the system of FIG. 2.

FIG. 1 is a front view of an embodiment of a heads-up display 100, in accordance with aspects of the inventive concept. FIG. 2 is a side view of an embodiment of a surgical heads-up display system 200 including the heads-up display 100 of FIG. 1, in accordance with aspects of the inventive concept. And FIG. 3 is a top view of the heads-up display system 200 of FIG. 2.

The system 200 comprises a heads-up display 100 and an articulable arm 150 coupled to the heads-up display. The heads-up display 100 is configured to receive a portable electronic device 10 (e.g., a smartphone) and to redirect a display output of the portable electronic device. The articulable arm 150 is configured to enable selective positioning and maintenance of the heads-up display 100 in a selected position such that the display output of the portable electronic device is redirected in a chosen direction (see FIGS. 2 and 3)—particularly for use by medical staff 8.

Referring to FIG. 1 and FIGS. 1A-1D, the heads-up display 100 includes a dock (or base) 102 configured to receive, support, and maintain the portable electronic device 10, so that the portable electronic device can be disposed, mounted, and/or maintained therein. In some embodiments, the portable electronic device 10 can be a smartphone, tablet, phablet, or similar device, as examples.

The dock can include a power source, such as a battery or AC power source configured to power the electronic device 10 and or heads-up display 100.

In some embodiments, the dock 102 can include a dock opening 104 configured to slidably receive the portable electronic device 10. In some embodiments, the dock opening 104 can be a side opening configured to laterally receive the portable electronic device, as in FIG. 1. In other embodiments, the dock opening 104 can be a top or bottom opening configured to longitudinally receive the portable electronic device 10.

In some embodiments, the dock 102 includes a support platform or structure configured to support to the portable electronic device. In various embodiments, the electronic device can be maintained within the dock 102 in a substantially horizontal position, with the display upward facing.

The dock 102 and/or the support platform 106 includes a camera opening (not visible) configured to reveal a camera of the portable electronic device when disposed and/or maintained in the dock 102. The camera opening enables the camera to be unobstructed when maintained in the dock 102. Therefore, the camera remains functional, e.g., to acquire images and/or video.

In some embodiments, the dock 102 can include a display frame 108 configured to form a display opening 108a revealing a display screen of the portable electronic device when disposed and/or maintained in the dock 102. Accordingly, output from the display can be transmitted to a display medium 120 of the heads-up display 100. The output from the display can be content from the camera or content from other sources, e.g., streaming content and/or the presentation of text, image, and/or video content stored locally and/or received from a network. Such network could include a wired or wireless connection, e.g., Wifi, cellular, Bluetooth, Internet, intranet, virtual private network, etc. In FIG. 1, a display output of a smartphone 10 maintained within base 102 is reflected by the display medium 120. The output is an output of a surgical procedure (see FIGS. 2 and 3) captured with the phone camera, output from the smart phone display, and reflected via the display medium 120.

In some embodiments, the dock 102 and/or the display frame 108 can include one or more audio transmission paths or openings 110 configured to receive audio output from the portable electronic device 10 in the dock 102 and to transmit the audio output external to the dock 102.

The heads-up display 100 display medium 120 can be configured to receive and redirect the display output from the portable electronic device 10 disposed or maintained in the heads-up display dock 102, as shown in FIG. 1. In some embodiments, the display medium 120 is configured to project the display output of the portable electronic device. In some embodiments, the display medium is configured to reflect the display output of the portable electronic device.

As examples, the display medium 120 can be or include one or more of a beam splitter, combiner glass, active mirror, passive mirror, semi-transparent mirror, an electrically switchable trans-reflective mirror, and/or remote display system.

As further illustrative examples, in some embodiments, the display medium 120 can be or include a beam splitter and/or collimator.

In some embodiments, the display medium 120 can be configured to close the display opening, such as by rotating toward and onto the display frame 108 (see FIG. 1). In some embodiments, the angle of the display medium 120 with respect to the display frame 108 can be user adjustable.

As a representative example, the display medium 120 can be configured for orientation at an angle of between about 0 and less than 90 degrees with respect to the display frame 108 or the display of the portable electronic device 10 disposed in the heads-up display. In some embodiments, the display medium 120 can be configured for orientation at an angle of between about 0 and about 60 degrees or less with respect to the display frame or the display of the portable electronic device disposed in the heads-up display. In some embodiments, the display medium can be configured for orientation at an angle of between about 0 and about 45 degrees or less with respect to the display frame or the display of the portable electronic device disposed in the heads-up display. In some embodiments, the display medium can be configured for orientation at an angle of between about 30 and about 60 degrees or less with respect to the display frame or the display of the portable electronic device disposed in the heads-up display. In some embodiments, the display medium can be configured for orientation at an angle of 45 degrees or about 45 degrees with respect to the display frame or the display of the portable electronic device disposed in the heads-up display.

In some embodiments, the display medium 120 is connected to the dock 102 and/or display frame 108 by at least one hinge 122. The hinge can include one or more preset stop positions for orienting the reflective medium at one or more predetermined angles. As an example, the hinge 122 can include a 0 degree or closed stop position (see FIG. 1). As another example, the hinge 122 can include a 45 degree stop position (see FIG. 1).

Figure 4:
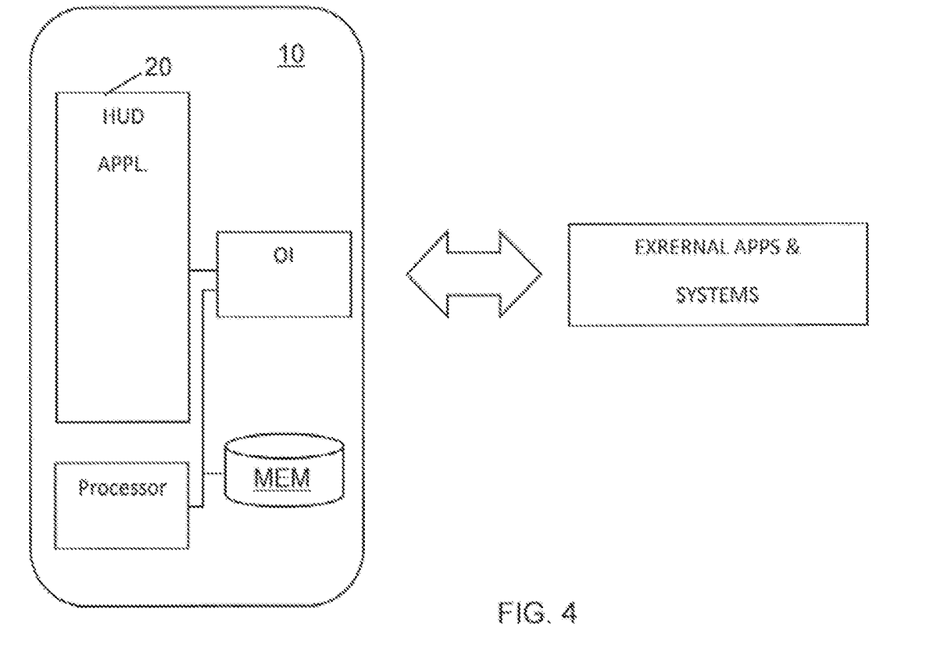
FIG. 4 is a block diagram of a portable electronic device having a "HUD" application, in accordance with aspects of the inventive concept.

Referring to FIG. 4, in some embodiments, the heads-up display system includes a surgical heads-up display computer program product and/or computer application 20 (collectively, "heads-up display application" or "HUD application") configured for storage on and execution by the portable electronic device 10, e.g., a smartphone.

Referring to FIGS. 2 and 3, in some embodiments, the articulable arm 150 can include a first end "A" coupled to the heads-up display 100. The first end A can be removably coupled to the heads-up display 100 such that the heads-up display can be used apart from the articulable arm 150. In some embodiments, an articulable joint couples the first end the articulable arm 150 to the heads-up display.

The articulable arm 150 can include a second end "B" distal from the first end A, the second end having a mount 152. In some embodiments, the mount 152 can be configured to couple to or be supported by a surface, structure, or apparatus. In some embodiments, the articulable arm second end mount 152 is a table mount, bed mount, cart mount, or wall mount, as examples. In some embodiments, an articulable joint couples the second end mount 152 with the articulable arm 150.

In some embodiments, the articulable arm second end mount 152 can be configured to removably attach to a patient support apparatus, such as a bed, chair, or table 250. In some embodiments, the articulable arm second end mount 152 can include or take the form of a clamp, such as a spring clamp, for example, a magnet, a suction cup, or openings for receiving bolts, screws, or other fasteners.

In some embodiments, the mount 152 can be configured to rest upon a surface. In such cases, the mount 152 can be relatively heavy such that the system is not unstable, e.g., between 5-10 lbs.

In some embodiments, the articulable arm can include two or more arm segments S1, S2 connected by one or more articulable joints J1. In some embodiments, the articulable arm 150 can include three or more arm segments S1, S2, S3 connected by two or more articulable joints J1, J2.

In some embodiments, the articulable arm 150 can include a post arm segment S3, coupled to the mount 152. In some embodiments, the post arm segment S3 is a height-adjustable post. In some embodiments, the height-adjustable post S3 is a telescoping post. In some embodiments, the post arm segment S3 is not rotatable with respect to the mount 152, while in other embodiments, the post arm segment can be rotatable with respect to the mount 152.

In some embodiments, the articulable joint or joints can enable up to a 360 degree rotation. In some embodiments, the articulable joint or joints can enable up to a 180 degree rotation. In some embodiments, the articulable joint or joints can enable two or more degrees of freedom. In some embodiments, the articulable joint or joints can include one or more hinge (e.g., a pin hinge) and/or one or more ball joint.

In some embodiments, the HUD application 20 (see FIG. 4) can be configured to enable voice command control of the portable electronic device. In some embodiments, the HUD application 20 can be configured to enable voice command control of the camera, display, applications, and/or communications of the portable electronic device. In some embodiments, the HUD application 20 can be configured to enable received text messages to be read out loud. In some embodiments, the HUD application 20 can be configured to enable phone calls to be made, conducted, and/or answered. In some embodiments, the HUD application 20 can be configured to enable voice to text messages to be generated and sent to contacts.

In still embodiments, the HUD application 20 can be configured to enable a light of the portable electronic device to be selectively turned on/off. In some embodiments, the HUD application 20 can be configured to enable pictures to be taken with a camera of the portable electronic device. In some embodiments, the HUD application 20 can be configured to enable video to be recorded with a camera of the portable electronic device. In some embodiments, the HUD application 20 can be configured to enable a camera of the portable electronic device to zoom in/out.

The HUD application 20 can further comprise a display transmission module configured to output all or a portion of the display of the docked electronic device 10 to one or more remote displays and/or display systems. The one or more remote displays and/or display systems can include a surgical microscope to add more magnification or transfer images to the microscope processing system. The display transmission module can be configured to enable the user (e.g., medical staff) to use the microscope for viewing and/or capturing images and/or video of the electronic device 10.

That is, the HUD application 20 can be configured such that, when installed and executing on a portable electronic device having at least one computer memory and processor, a user can control and/or manage operations of the device, including one or more of the functions of the electronic device described herein.

In various embodiments, such as a surgical setting, it can be preferable, if not essential, for the heads-up display system to be provided as a sterile apparatus. In such cases, the articulable arm and/or heads-up display can be formed of a sterile material, or a material capable of sterilization. In some embodiments, sterilized pouches, wraps, draping, material, or other compartment can be used for achieving and maintaining sterility, e.g., by covering all or part(s) of the heads-up display system, particularly in the treatment zone (or sterile field). In some embodiments, the dock can form an enclosure that can receive and enclose an unsterile portable electronic device with the external surfaces of the system being sterile.

In preferred embodiments, the heads-up display system can be configured to avoid and shield against electromagnetic radiation, e.g., by preventing interference caused by the portable electronic device. In such a case, the heads-up display and/or dock and have or be EMI shielding.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

APPENDIX

Attached, as part of this specification, is a series of pictures demonstrating use of an embodiment of a surgical heads-up display system, in accordance with aspects of the inventive concept.

What is claimed is:

1. A surgical heads-up display system comprising:
    a heads-up display (HUD) that includes a dock configured to receive and maintain a smartphone and/or tablet in substantially horizontal position that leaves a downward-facing camera and an upward-facing display of the smartphone unobstructed, the HUD further including a display medium that projects or redirects a display output of the smartphone and/or tablet; and
    an articulable arm having at least one articulable joint, and having a first end configured to couple to the heads-up display and a second end mount to configured to couple to a treatment surface, including an operating table, wherein the articulable arm is configured to enable positioning and maintenance of the heads-up display in a selected position relative to the treatment surface,
    wherein the articulable arm includes a first arm segment comprising the first end and a second arm segment comprising the second end, wherein the first and second arm segments are joined by an articulable joint from the at least one articulable joint, and the articulable joint enables three or more degrees of rotational freedom of the first arm segment with respect to the second arm segment.

2. The system of claim 1, wherein the articulable arm includes a first end removably coupled to the heads-up display.

3. The system of claim 1, wherein the articulable arm second end mount is configured to rest upon a surface.

4. The system of claim 1, wherein the articulable arm second end mount is configured to couple to a surface, structure, or apparatus.

5. The system of claim 1, wherein the second end mount includes a table mount, bed mount, cart mount, or wall mount.

6. The system of claim 1, wherein the second end mount includes a clamp.

7. The system of claim 1, further comprising:
    an articulable joint coupling the second end mount with the articulable arm.

8. The system of claim 1, wherein the articulable arm includes two or more arm segments connected by one or more articulable joint.

9. The system of claim 1, wherein the articulable arm includes three or more arm segments connected by two or more articulable joints.

10. The system of claim 1, wherein the articulable arm second end includes a post arm segment.

11. The system of claim 10, wherein the post arm segment is a substantially vertical post.

12. The system of claim 11, wherein the post arm segment is a height-adjustable post.

13. The system of claim 12, wherein the height-adjustable post is a telescoping post.

14. The system of claim 10, wherein the post arm segment is not rotatable with respect to the second end mount.

15. The system of claim 10, wherein the post arm segment is rotatable with respect to the mount.

16. The system of claim 1, wherein the at least one articulable joint enables up to a 360 degree rotation of the HUD relative to the treatment surface.

17. The system of claim 1, wherein the display medium is configured for orientation at an angle of between about 0 and about 60 degrees or less with respect to the display frame or the display of the portable electronic device disposed in the heads-up display.

18. The system of claim 1, wherein the system includes:
    a surgical heads-up display computer program product ("HUD application") configured for storage on and execution by the smartphone and/or tablet to a least partially control function of the camera and/or the display of the smartphone and/or tablet.

19. The system of claim 18, wherein the HUD application enables, in response to a voice control command, one or more of:
    received text messages to be read out loud;
    phone calls to be placed, conducted, and/or answered;
    voice to text messages to be generated and sent to contacts;
    a light of the portable electronic device to be selectively turned on/off;
    pictures to be taken with a camera of the portable electronic device;
    video to be recorded with a camera of the portable electronic device, and/or
    a camera of the portable electronic device to zoom in/out.

* * * * *